US009918693B2

(12) United States Patent
Gotanda

(10) Patent No.: US 9,918,693 B2
(45) Date of Patent: Mar. 20, 2018

(54) X-RAY CT APPARATUS

(71) Applicant: TOSHIBA MEDICAL SYSTEMS CORPORATION, Otawara-Shi (JP)

(72) Inventor: Katsumi Gotanda, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/701,741

(22) Filed: May 1, 2015

(65) Prior Publication Data
US 2015/0320366 A1    Nov. 12, 2015

(30) Foreign Application Priority Data
May 12, 2014    (JP) ................................. 2014-098590

(51) Int. Cl.
| G01D 18/00 | (2006.01) |
|---|---|
| A61B 6/00 | (2006.01) |
| G01M 1/36 | (2006.01) |
| A61B 6/03 | (2006.01) |

(52) U.S. Cl.
CPC ............... *A61B 6/54* (2013.01); *A61B 6/035* (2013.01); *A61B 6/447* (2013.01); *G01M 1/36* (2013.01)

(58) Field of Classification Search
CPC ...... A61B 2090/5025; A61B 2090/504; A61B 6/547; A61B 6/54; A61B 6/548; A61B 6/584
USPC .......................................................... 378/87
See application file for complete search history.

(56) References Cited

U.S. PATENT DOCUMENTS

| 2002/0039403 A1* | 4/2002 | Oota ...................... A61B 6/032 378/196 |
|---|---|---|
| 2007/0041488 A1* | 2/2007 | Hoheisel ................ A61B 6/035 378/4 |
| 2011/0069819 A1* | 3/2011 | Urban .................... A61B 6/547 378/197 |
| 2011/0263364 A1* | 10/2011 | Klarer ...................... F16H 9/24 474/70 |
| 2013/0259199 A1* | 10/2013 | Ueji ................. G01N 23/20008 378/70 |
| 2013/0308759 A1* | 11/2013 | Pettinato ................ A61B 6/035 378/207 |

(Continued)

FOREIGN PATENT DOCUMENTS

| JP | 2001-170038 | 6/2001 |
|---|---|---|
| JP | 2001-276039 | 10/2001 |

(Continued)

*Primary Examiner* — Jason McCormack
(74) *Attorney, Agent, or Firm* — Oblon, McClelland, Maier & Neustadt, L.L.P.

(57) ABSTRACT

According to one embodiment, an X-ray CT apparatus includes a rotating body configured to house an X-ray tube which irradiates X-rays on an object; at least one weight configured to be housed in the rotating body and to adjust balance of the rotating body; a sensor configured to detect fluctuation amount in a front-back direction approximately orthogonal to a rotating surface of the rotating body; processing circuitry configured to determine moving amount of the weight based on the fluctuation amount in a front-back direction detected by the sensor; and at least one weight moving mechanism configured to be housed in the rotating body and to move a position of the weight based on the moving amount determined by the determination unit.

11 Claims, 9 Drawing Sheets

(56) References Cited

U.S. PATENT DOCUMENTS

2014/0163734 A1\* 6/2014 Bier .................. B25J 9/1633
   700/258

FOREIGN PATENT DOCUMENTS

| JP | 2005-211660 | 8/2005 |
| JP | 2006-212421 | 8/2006 |
| JP | 2009-162655 | 7/2009 |

\* cited by examiner

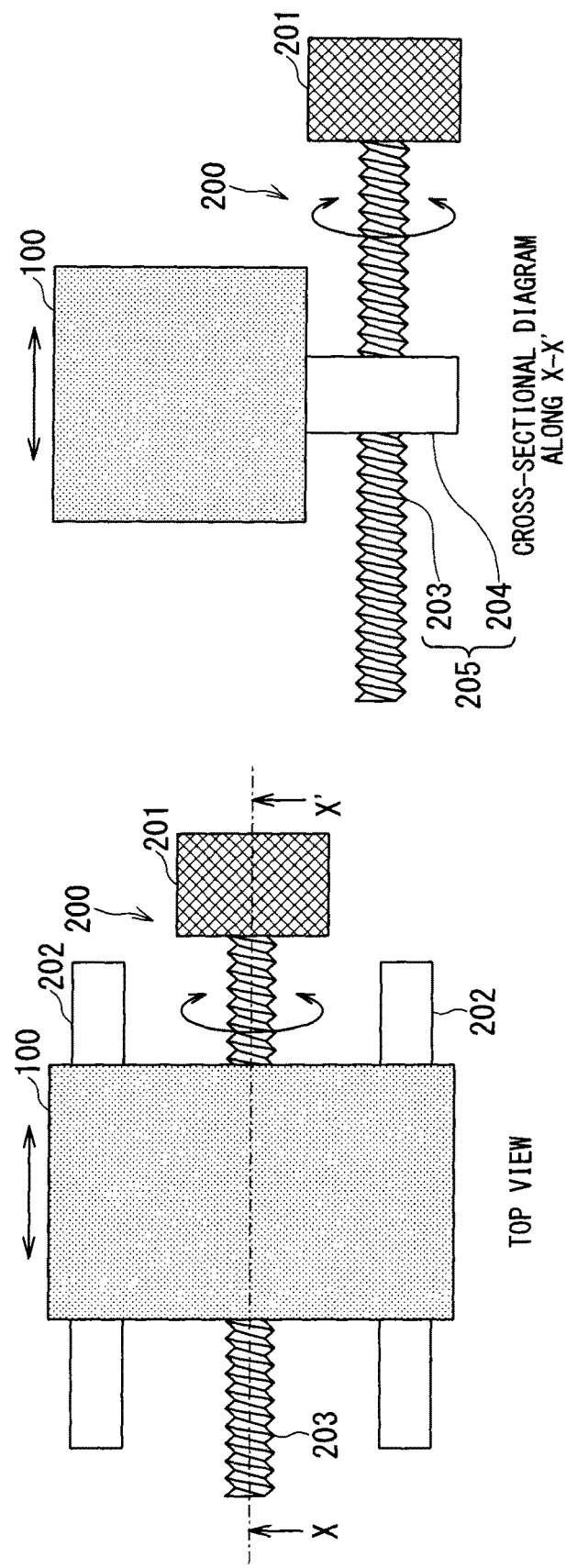

TOP VIEW

X-RAY CT APPARATUS

CROSS-REFERENCE TO RELATED APPLICATION

This application is based upon and claims the benefit of priority from Japanese Patent Application No. 2014-98590, filed on May 12, 2014, the entire contents of which are incorporated herein by reference.

FIELD

Embodiments described herein relate generally to an X-ray CT (Computed Tomography) apparatus.

BACKGROUND

In an X-ray CT apparatus, projection data of many two-dimensional images are acquired by rapidly rotating an X-ray source and an X-ray detector around an object (patient) while moving a table with the object loaded thereon in the rotation axis direction. Then, a three-dimensional image of the object is obtained by reconstructing the acquired many projection data.

In an X-ray CT apparatus, a rotating body, which houses various types of units such as a high voltage power source and a DAS (Data Acquisition System) aside from an X-ray source and an X-ray detector, rotates around an object at high speed. If the rotating body vibrates due to the rotational motion, or if the rotational motion becomes imbalanced, image quality deteriorates because the position of the X-ray detector fluctuates.

In order to reduce such vibration of the rotating body and imbalance of the rotational motion, technology to enhance strength and rigidity of a gantry supporting the rotating body has been considered.

Meanwhile, a weight for adjusting balance of the rotating body (i.e. eliminating imbalance of the rotating body) is disposed inside the rotating body, in addition to the aforementioned respective units. In the conventional balance adjustment method, imbalance is eliminated by adjusting heaviness of the weight and the position of the weight after assembling the gantry.

In the conventional balance adjustment method, firstly, measurement equipment for measuring fluctuation in rotation is attached by user operation, and then the heaviness of the weight and the position of the weight are adjusted on the basis of the measurement result by user operation as well. In order to appropriately determine the heaviness of the weight and the position of the weight, highly advanced skills are required for an operator.

In addition, balance adjustment is also required in the case of replacing a unit in the rotating body due to malfunction or the like, and thus, attaching and detaching of the measurement equipment, as well as adjusting the heaviness of the weight and the position of the weight are required each time of replacement.

Accordingly, an X-ray CT apparatus which can accurately adjust rotational balance in a short time without relying on skills of an operator has been desired.

BRIEF DESCRIPTION OF THE DRAWINGS

In the accompanying drawings:

FIG. 3A is a schematic top view showing a configuration example of a weight and a weight moving mechanism;

FIG. 3B is a schematic cross-sectional diagram along the chain line X-X' shown in FIG. 3A;

DETAILED DESCRIPTION

According to one embodiment, an X-ray CT apparatus includes a rotating body configured to house an X-ray tube which irradiates X-rays on an object; at least one weight configured to be housed in the rotating body and to adjust balance of the rotating body; a sensor configured to detect fluctuation amount in a front-back direction approximately orthogonal to a rotating surface of the rotating body; processing circuitry configured to determine moving amount of the weight based on the fluctuation amount in a front-back direction detected by the sensor; and at least one weight moving mechanism configured to be housed in the rotating body and to move a position of the weight based on the moving amount of the weight determined by the determination unit.

Embodiments of an X-ray CT apparatus will be explained with reference to the accompanying drawings.

(1) Overall Structure and Overall Operation

Figure 1:
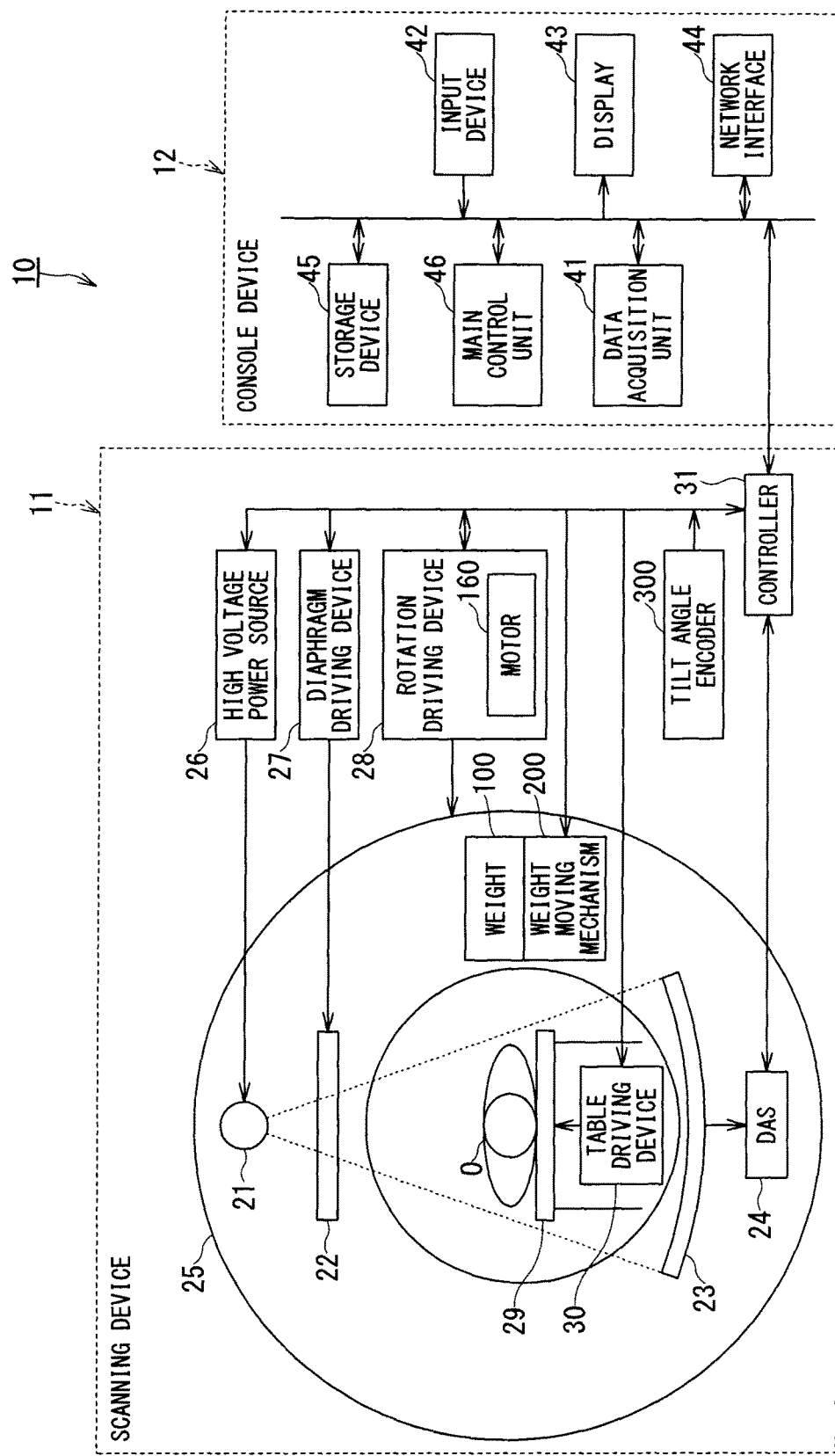
FIG. 1 is a schematic entire configuration diagram showing an example of an X-ray CT apparatus of one embodiment.

FIG. 1 is a schematic entire configuration diagram showing an example of an X-ray CT apparatus according to one embodiment of the present invention. The X-ray CT apparatus 10 includes a scanning device 11 and a console device 12. The scanning device 11 of the X-ray CT apparatus 10 is normally installed in an examination room and is configured to generate X-ray projection data of an imaging part of a patient O (object). The scanning device 11 is also referred to as a gantry.

On the other hand, the console device 12 is normally installed in a control room adjacent to the examination room. The console device 12 performs generation and display of a three-dimensional image by reconstructing projection data around the object outputted from the scanning device 11, in addition to control of the entirety of the X-ray CT apparatus 10. In addition, the console device 12 of the present embodiment performs processing relevant to balance adjustment of the rotating body 25, as described below.

The scanning device 11 of the X-ray CT apparatus 10 includes an X-ray tube (X-ray source) 21, a diaphragm 22, an X-ray detector 23, a DAS (Data Acquisition System) 24, a rotating body 25, a high voltage power source 26, a diaphragm driving device 27, a rotation driving device 28, a table 29, a table driving device 30, at least one weight 100, at least one weight moving mechanism 200, a tilt angle encoder 300 and a controller 31.

The X-ray tube 21 generates X-rays when a voltage (hereinafter referred to as a tube voltage) is applied from the high voltage power source 26. The X-rays generated by the X-ray tube 21 are irradiated toward the patient O as fan beam X-rays or cone beam X-rays.

The diaphragm 22 is controlled by the controller 31 via the diaphragm driving device 27, and adjusts the irradiation range of X-rays irradiated from the X-ray tube 21 in the slice direction.

The X-ray detector 23 is constituted of one or a plurality of X-ray detecting elements (charge storage elements). These X-ray detecting elements detect X-rays irradiated from the X-ray tube 21. The X-ray tube 21 and the X-ray detector 23 are supported by the rotating body 25 so as to face each other, placing the patient O loaded on the table 29 therebetween.

As the X-ray detector 23, for example, a so-called one one-dimensional array-type detector, i.e., a single slice type detector, which includes plural channels of the X-ray detecting elements in a channel direction, while including a single row of the X-ray detecting elements in a slice direction can be used. Alternatively, as the X-ray detector 23, a two-dimensional array-type detector (multi-slice type detector) in which a plurality of the X-ray detecting elements are arrayed in the channel direction and a plurality of rows of the X-ray detecting elements are arrayed in the slice direction can be used.

The DAS 24 amplifies signals of the transmission data detected by the respective X-ray detecting elements constituting the X-ray detector 23, converts the amplified signals into digital signals, and outputs them as the projection data. These data outputted from the DAS 24 are inputted to the console device 12 via the controller 31 of the scanning device 11.

The high voltage power source 26 supplies the X-ray tube 21 with electric power required for irradiation of X-rays, under the control of the controller 31. The diaphragm driving device 27 adjusts the X-ray irradiation range in the slice direction by controlling the opening of the diaphragm 22, under the control of the controller 31.

The rotating body 25 houses the X-ray tube 21, the high voltage power source 26, the diaphragm 22, the diaphragm driving device 27, the X-ray detector 23, the DAS 24, etc, and integrally supports these components. The controller 31 controls the rotation driving device 28 so as to rotate the rotating body 25, and thereby the X-ray tube 21, the diaphragm 22, the X-ray detector 23 and the DAS 24 integrally rotate around the patient O. Incidentally, each of the above components, which are housed in the rotating body 25 for obtaining the X-ray projection data and rotate integrally with the rotating body 25, is hereinafter referred to as a rotating body component 150.

In addition, the rotating body 25 houses one or more weight(s) 100 for adjusting balance and one or more weight moving mechanism(s) 200 for moving the position of the weight(s) 100, in addition to the above rotating body component 150. The structure and operation of the weights 100 and the weight moving mechanism(s) 200 will be described below.

The rotation driving device 28 is configured to include, for example, the motor 160 of a direct drive type. The motor 160 is controlled by the controller 31 so as to rapidly rotate the rotating body 25 around the bore at a high rate of, for example, one revolution in 0.5 second or shorter.

The table 29 is configured to be able to load the patient O. The table driving device 30 moves the table 29 upward and downward under control of the controller 31. In addition, the table driving device 30 is controlled by the controller 31 so as to move the table 29 to an X-ray irradiation field of the bore of the central part of the rotating body 25.

The controller 31 is configured to include processing circuitry or a CPU (Central Processing Unit) and storage media such as a RAM (Random Access Memory) and a ROM (Read Only Memory), and makes the X-ray CT apparatus 10 perform a scan by controlling the X-ray detector 23, the DAS 24, the high voltage power source 26, the diaphragm driving device 27, the rotation driving device 28 and the table driving device 30 in accordance with a program stored in the storage media. The RAM of the controller 31 provides a work area that temporarily stores data and programs performed by the CPU. The storage media of the controller 31 including the ROM stores a startup program of the scanning device 11, a control program of the scanning device 11 and various types of data required for executing these programs.

Incidentally, the storage media of the controller 31 such as the ROM and RAM may be a magnetic or optical storage medium or a semiconductor memory, etc., which are readable by the processing circuitry or the CPU. Alternatively or in combination, all or a part of the programs and data may be downloaded via an electronic network.

On the other hand, the console device 12 of the X-ray CT apparatus 10 is configured, for example, as a computer and can transmit/receive data to/from a network such as a LAN (Local Area Network) of hospital facilities.

The console device 12 includes a data acquisition unit 41, an input device 42, a display 43, a network interface 44, a storage device (memory circuitry) 45 and a main control unit (processing circuitry or a CPU) 46, as shown in FIG. 1.

The data acquisition unit 41 acquires the projection data obtained in a scan performed by the scanning device 11 via the DAS 24 and the controller 31. The projection data acquired by data acquisition unit 41 are stored in the storage device 45. The data acquisition unit 41 may be implemented by the processing circuitry or the CPU executing a specific program further stored in the storage device 41.

The input device 42 may be configured, for example, as a general input device such as a keyboard, a touch panel a numerical keypad, a mouse, etc. and outputs operational input signals in accordance with operation by a user to the main control unit 46.

The display 43 may be configured, for example, as a general display device such as a liquid crystal display, an OLED (Organic Light Emitting Diode), etc. and displays various types of images such as a scanogram or a reconstructed image under control of the main control unit 46.

The network interface 44 implements various information communication protocols in accordance with a type of a network. The network interface 44 connects the console device 12 to other electrical equipments in accordance with these various protocols. Electrical connection via an electronic network etc. can be applied to this connection. The above electronic network means general information communication networks using telecommunications technology and includes a telephone communication channel network, an optical fiber communication network, a cable communication network, a satellite communication, etc. aside from the internet network and a wireless/wired LAN such as a LAN of hospital facilities.

The storage device 45 may be configured as a storage medium readable by the CPU of the main control unit 46 such as a magnetic or optical storage medium or a semiconductor memory, etc. The storage device 45 stores the projection data acquired by the data acquisition unit 41 etc. and further stores programs for achieving various functions performed by the processing circuitry or the CPU of the main control unit 46. The number of the processing circuitry or the CPU is not limited to one. Plural processing circuitries or plural processors may be included in the main control unit 46.

(2) Balance Adjustment

As mentioned above, in the X-ray CT apparatus 10 of the present embodiment, the weight(s) 100 for balance adjustment of the rotating body 25 and the weight moving mechanism(s) 200 which moves the position of the weight(s) 100 are housed in the rotating body 25.

Figure 2B:
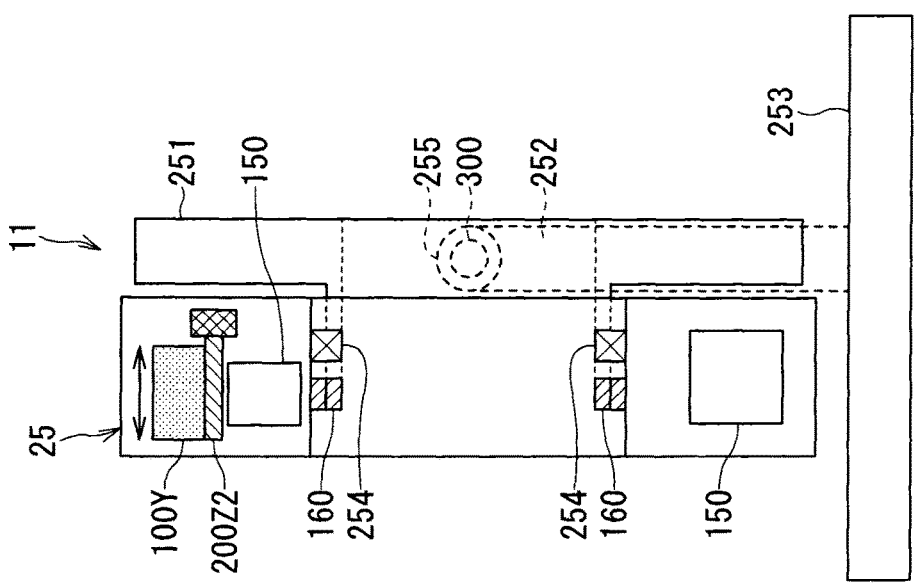
FIG. 2B is a diagram showing the structural outline of the rotational structure of the scanning device and the example of arrangement of weights and weight moving mechanisms shown in FIG. 2A, when viewed from the side.
Figure 2A:
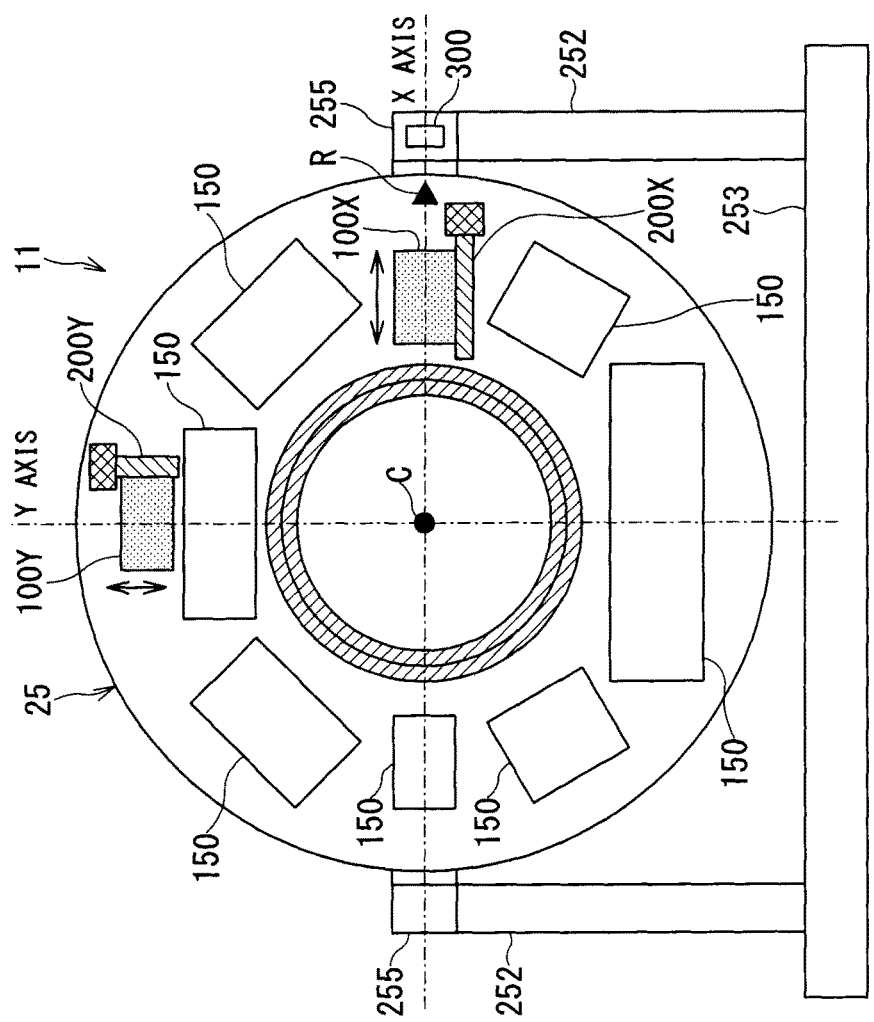
FIG. 2A is a diagram showing a structural outline of the rotational structure of a scanning device and an example of arrangement of weights and weight moving mechanisms, when viewed from the front.

FIG. 2A and FIG. 2B are diagrams showing a structural outline of the rotational structure of the scanning device 11 including the rotating body 25 and also showing an example of arrangement of the weight(s) 100 and the weight moving mechanism(s) 200. FIG. 2A is a diagram showing an outline arrangement of the scanning device 11 when viewed from the front, and FIG. 2B is a diagram showing an outline arrangement of the scanning device 11 when viewed from the side.

The scanning device 11 includes the rotating body 25, a fixed body 251 disposed on the rear side of the rotating body 25, the supporting structure 252 that supports the fixed body 251 from the right and left sides, and the base 253 installed on the floor for fixing the supporting structure 252.

A ring bearing 254 is disposed between the rotating body 25 and the fixed body 251, and the fixed body 251 rotatably supports the rotating body 25 with this ring bearing 254. Moreover, the ring-shaped motor 160 of a direct drive type is disposed between the rotating body 25 and the fixed body 251. The motor 160 rotates the rotating body 25 about the rotation center C at high speed. The monitoring value of the drive current of the motor 160 is outputted to the console device 12 via the controller 31.

Incidentally, as an alternative aspect, a normal motor 160 which drives a timing belt wound around the circumference of the rotating body 25 may be provided, instead of the direct drive type motor.

A tilt bearing 255 is disposed between the fixed body 251 and the supporting structure 252. The rotating body 25 and the fixed body 251 are integrally rotated about the center of the tilt bearing 255 in the tilt direction. A tilt angle encoder 300 is disposed adjacent to the tilt bearing 255, and the monitoring value of the tilt angle of the rotating body 25 is outputted from the tilt angle encoder 300 to the console device 12 via the controller 31.

The rotating body 25 houses the rotating body components 150 such as the X-ray tube 21, the high voltage power source 26, the diaphragm 22, the diaphragm driving device 27, the X-ray detector 23, the DAS 24 and so on. In FIG. 2A and FIG. 2B, these rotating body components 150 are schematically illustrated with white boxes.

Moreover, the rotating body 25 houses the weights 100 (100X and 100Y) and the weight moving mechanisms 200 (200X and 200Y). Although the number of the weights 100 and the number of the weight moving mechanisms 200 are respectively two in the example of FIG. 2A and FIG. 2B, their number is not limited to two. The number of the weight(s) 100 or the weight moving mechanisms 200 may be one, three, or more than three.

In addition, the arrangement of the weights 100 and the weight moving mechanisms 200 is not limited to the embodiment shown in FIG. 2A and FIG. 2B. In FIG. 2A, the reference position R of the rotational direction of the rotating body 25 is illustrated with a black triangle mark. It is assumed that the reference position R is located on the right side in the horizontal direction (X axis direction) when the rotation of the rotating body 25 is stopped. At this state, out of the weights 100A and 100B, one is disposed so as to be located approximately on the X axis and the other is disposed so as to be located approximately on the Y axis in the example of FIG. 2A. Then, the position of each of the weights 100X and 100Y can be independently adjusted in the illustrated arrow direction (the radial direction of the rotating body 25) by the weight moving mechanisms 200X and 200Y.

Fluctuation in the rotating surface caused by imbalance in the rotating surface can be suppressed by adjusting the respective positions of the weights 100X and 100Y in the two mutually independent directions (for example, two mutually orthogonal radial directions as shown in FIG. 2A).

On the other hand, if there is imbalance in the direction orthogonal to the rotating surface (hereinafter, referred to as the front-back direction or the Z axis direction), fluctuation about a tilt axis, i.e., fluctuation in the front-back direction may occur due to the rotational motion of the rotating body 25. The X-ray CT apparatus 10 of this embodiment includes weight moving mechanisms 200Z1 and 200Z2 which respectively move the positions of the weights 100X and 100Y in the Z axis direction as shown in FIG. 2B. In FIG. 2B, only the weight 100Y and the weight moving mechanism 200Z2 are illustrated. The weight moving mechanisms 200X, 200Y, 200Z1 and 200Z2 may be integrally referred to as a weight moving unit.

The weight moving mechanism 200Z2 integrally moves the weight 100Y and the weight moving mechanism 200Y in the front-back direction. Similarly, the weight moving mechanism 200Z1 integrally moves the weight 100X and the weight moving mechanism 200X in the front-back direction.

Incidentally, one weight 100 movable in the radial direction and another weight 100 movable in the front-back direction may be separately disposed. In this case, the position of the weight 100 (first weight) which is made to move in the radial direction and the position of the other weight 100 (second weight) which is made to move in the front-back direction are respectively adjusted by separate weight moving mechanisms 200.

FIG. 3A is a schematic top view showing a configuration example of a weight 100 and a weight moving mechanism 200, and FIG. 3B is a schematic cross-sectional diagram along the chain line X-X' shown in FIG. 3A. The weight moving mechanism 200 includes an adjusting motor 201, guide members 202 and a motion convertor 205. The adjusting motor 201 rotates in the forward or reverse direction by the rotational amount defined on the basis of the moving amount determined by a moving amount determination unit 500 (see later-described FIG. 5) of the console device 12. The guide members 202 slidably support the weights 100 in its moving direction.

The motion convertor 205 converts the rotational motion of the adjusting motor 201 into linear motion. The motion convertor 205 is configured, for example, as a combination of a ball screw 203 and a slider 204. As shown in FIGS. 3A and 3B, one end of the ball screw 203 is connected to the adjusting motor 201, while a nut which meshes with the ball screw 203 is formed inside the slider 204

The motion convertor 205 is not limited to the combination of the ball screw 203 and the slider 204. Alternatively, the motion convertor 205 may be configured, for example, as a crank mechanism or a rack-pinion mechanism.

While adjusting the balance, the weight 100 is moved by the weight moving mechanisms 200 in the radial direction of the rotating body 25 or in the front-back direction.

On the other hand, after the balance adjustment is completed, the position of the weights 100 needs to be fixed, not to be changed even while the rotating body 25 is rotating.

Figure 4:
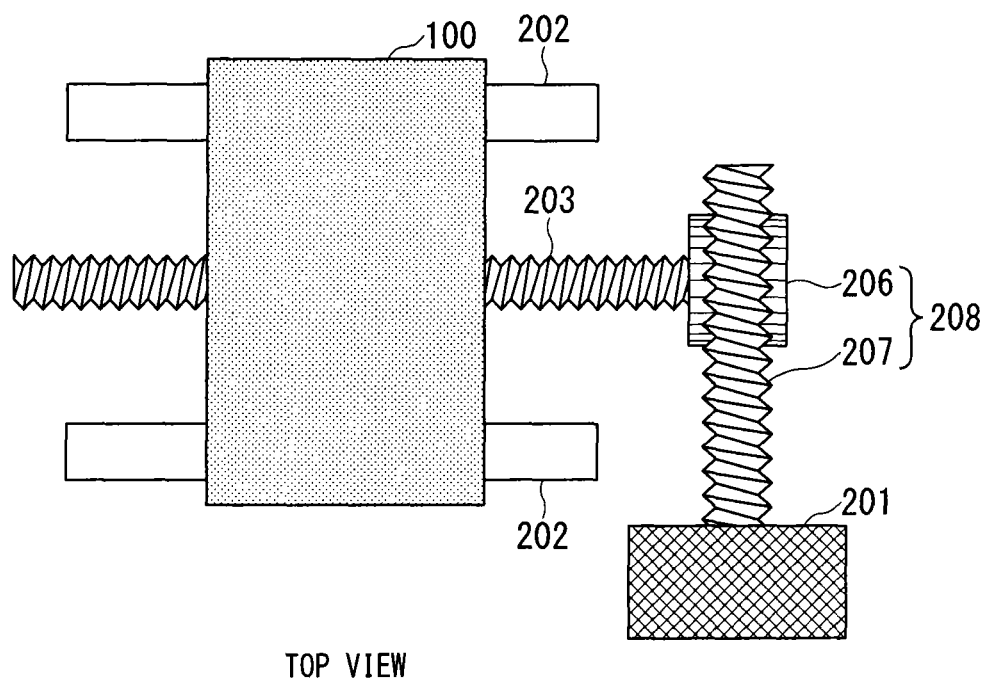
FIG. 4 is a diagram showing a configuration example of a weight moving mechanism in which a worm gear having a self-locking function is used.

FIG. 4 is a diagram showing an example of an embodiment in which a worm gear 208 having a self-locking function is used as the means for fixing the weight 100. In this embodiment, a worm wheel 206 of the worm gear 208 is fixed to one end of the ball screw 203, and a worm 207 of the worm gear 208 is connected and fixed to the rotary shaft of the adjusting motor 201. Further, the worm wheel 206 and the worm 207 are configured to mesh with each other. In this configuration, the rotation of the adjusting motor 201 is transmitted to the ball screw 203 via the worm gear 208, causing the weight 100 to move in the radial direction of the rotating body 25 or in the front-back direction. By contrast, because the worm gear 208 has a self-locking function, the weight 100 never moves by external force such as centrifugal force etc. in either case when the power of the adjusting motor 201 is on or off.

Because the fixing means using the worm gear 208 with a self-locking function does not need any user operation for fixing the position of the weight 100, it is an effective method in terms of work efficiency.

Instead of the above fixing means, the weight 100 and the housing frame of the rotating body 25 may be fixed to each other by using another fixing means such as bolts, after the balance adjustment is completed. In this method, though a user operation is required, the weights 100 can be more firmly fixed with a low-cost fixing means. As a further alternative fixing means, the adjusting motor 201 having a holding torque large enough not to be moved during a high speed rotation may be used.

Next, processing of controlling the aforementioned weight(s) 100 and the weight moving mechanism(s) 200 and adjusting the balance of the rotating body 25 will be explained.

Figure 5:
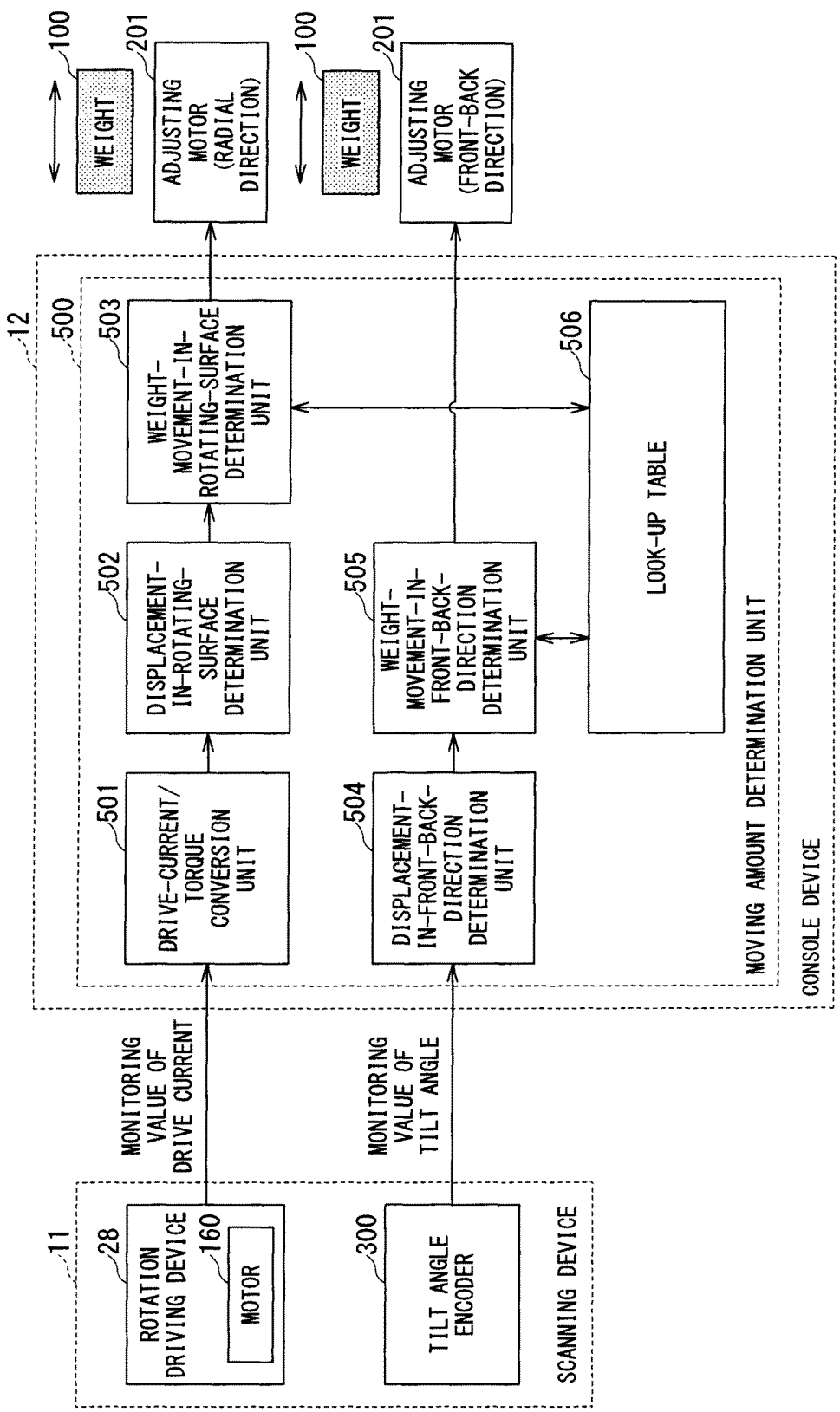
FIG. 5 is a block diagram showing a configuration example related to balance adjustment processing.
Figure 6:
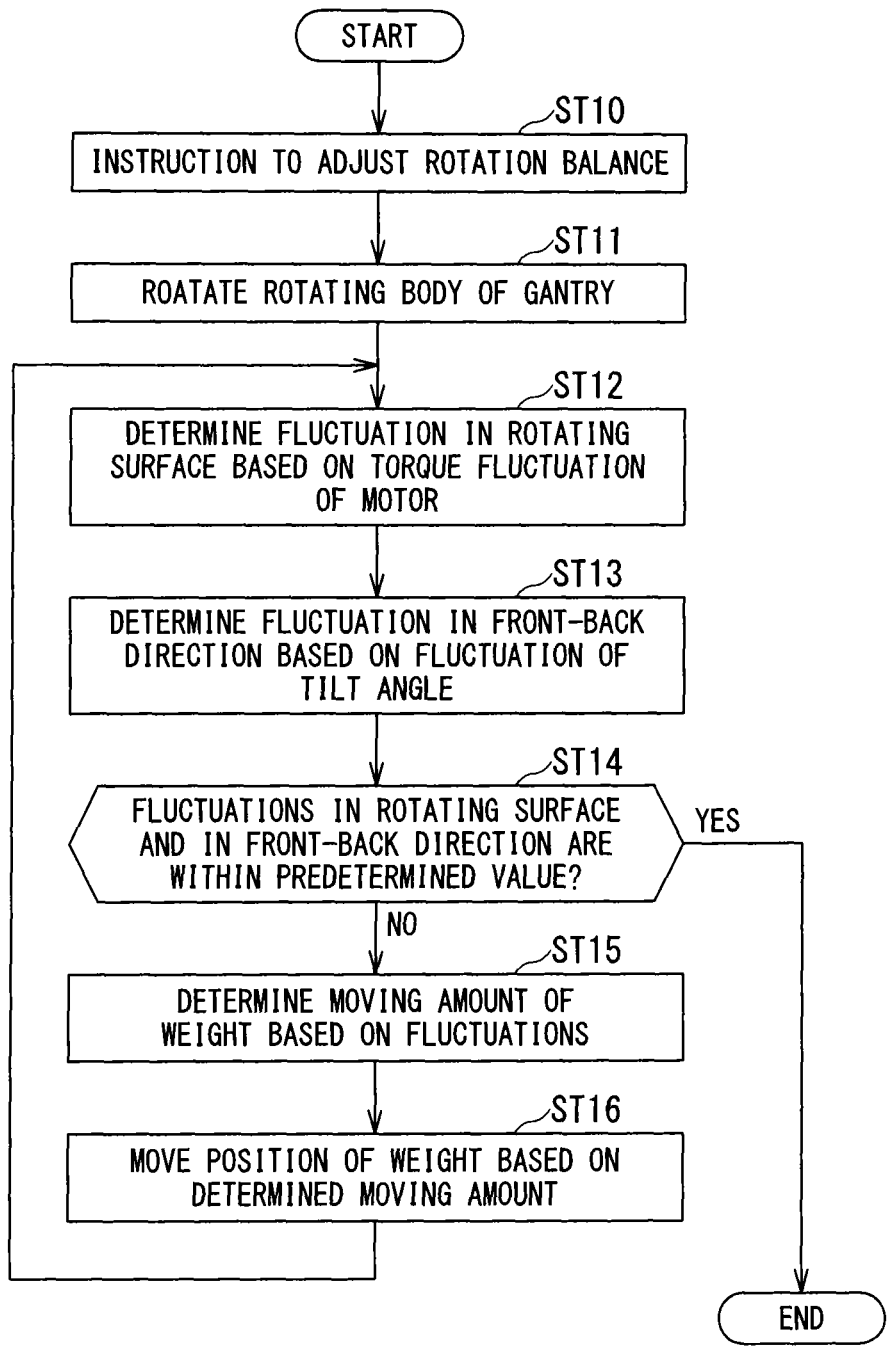
FIG. 6 is a flowchart showing the flow of the balance adjustment processing.

FIG. 5 is a block diagram showing a configuration example related to the balance adjustment processing, and FIG. 6 is a flowchart showing the flow of the balance adjustment processing.

Out of the components related to the balance adjustment processing, the processing of the moving amount determination unit 500 shown in FIG. 5 is achieved by executing a predetermined program stored in the storage device 45, and this predetermined program is executed by the processing circuitry or the CPU of the main control unit 46 of the console device 12. Instead of such software processing, the balance adjustment processing may be performed by using hardware such as ASIC (Application Specific Integrated Circuits) and so on. Alternatively, the balance adjustment processing may be performed by combining software and hardware.

The moving amount determination unit 500 is configured to include a drive-current/torque conversion unit 501, a fluctuation-in-rotating-surface determination unit 502, a weight-movement-in-rotating-surface determination unit 503, a fluctuation-in-front-back-direction determination unit 504, a weight-movement-in-front-back-direction determination unit 505 and a look-up table 506. The processing or the functions of each of units 501 through 505 can be implemented by the processing circuitry or the CPU executing one or more programs stored in the storage device 45.

The processing performed by each of the above units will be explained in accordance with the flowchart in FIG. 6. In the step ST10 of FIG. 6, an instruction to adjust the rotational balance is inputted via the input device 42 of the console device 12. As soon as the instruction to adjust the rotational balance is inputted, the console device 12 rotates the rotating body 25 via the controller 31 of the gantry (the scanning device 11) in the step ST11.

Next, in the step ST12, "fluctuation amount" (hereafter, referred to as simply "fluctuation") in the rotating surface is determined on the basis of the torque fluctuation of the motor 160 for rotational motion, as follows.

While the rotating body 25 is rotating, the monitoring value of the drive current is inputted from the motor 160 of the rotation driving device 28 to the drive-current/torque conversion unit 501 of the moving amount determination unit 500 of the console device 12. The motor 160 has predetermined characteristics of drive current versus torque. The drive-current/torque conversion unit 501 converts the monitoring value of the drive current into torque on the basis of the characteristics of drive current to torque.

Figure 7A:
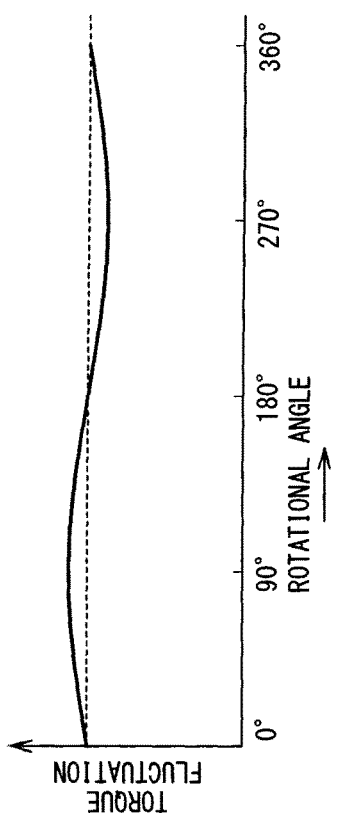
FIG. 7A to FIG. 7D are diagrams for explaining the concept of the balance adjustment in the rotating surface achieved on the basis of torque fluctuation amount.

FIG. 7A to FIG. 7D are diagrams for explaining the concept of the balance adjustment in the rotating surface achieved on the basis of the torque fluctuation. As illustrated in FIG. 7A, when balance in the rotating surface is perfectly adjusted, torque shows a constant value at any rotational angle as shown by the dashed straight line in FIG. 7A. However, when the balance in the rotating surface is imperfect, torque fluctuates as shown by the solid curve line in FIG. 7A.

The fluctuation-in-rotating-surface determination unit 502 determines fluctuation in the rotating surface on the basis of the torque fluctuation. There is a predetermined correspondence relation between the torque fluctuation and the fluctuation in the rotating surface. Thus, if the torque fluctuation is obtained, the fluctuation in the rotating surface can be determined.

Figure 7B:
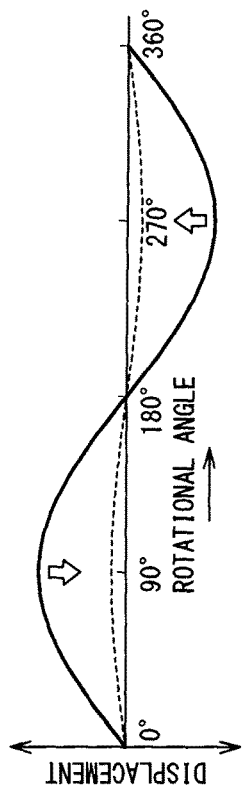
Figure 7C:
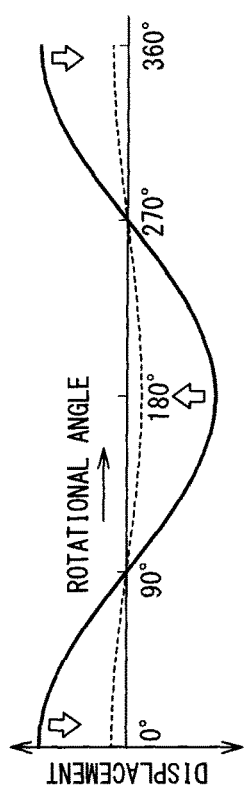
Figure 7D:
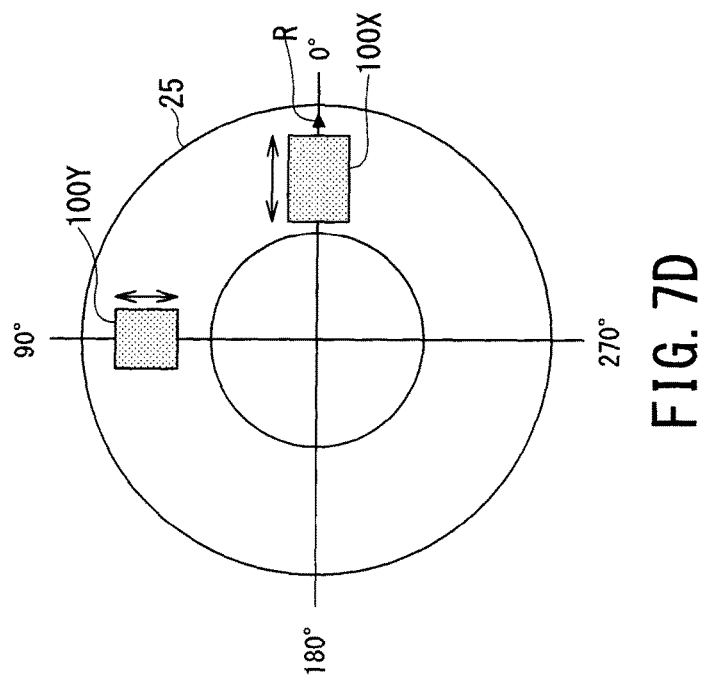

The displacement amount in the rotating surface due to imbalance (for example, the displacement amount in the right to left direction in FIG. 7D) fluctuates, for example, approximately in a sine wave shape in accordance with the rotational angle of the rotating body 25, as shown in FIG. 7B and FIG. 7C.

Meanwhile, in the step ST13, the monitoring value of the tilt angle outputted from the tilt angle encoder 300 of the scanning device 11 is inputted to the fluctuation-in-front-back-direction determination unit 504, and the fluctuation-in-front-back-direction determination unit 504 determines the fluctuation of the rotating body 25 in the front-back-direction on the basis of the fluctuation of the tilt angle.

Figure 8A:
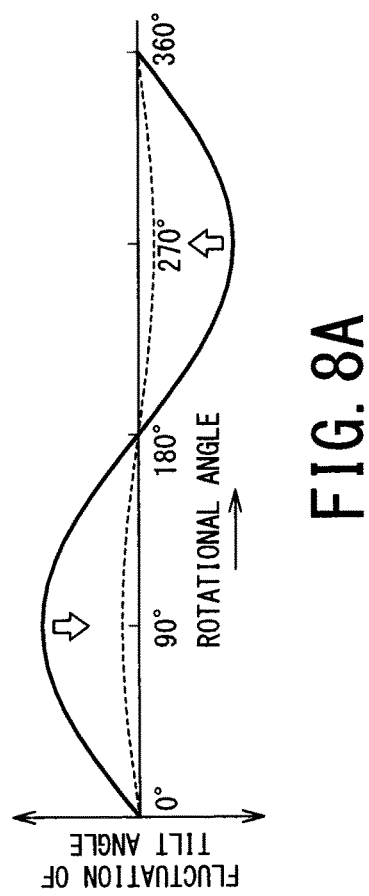
FIG. 8A to FIG. 8C are diagrams for explaining the concept of the balance adjustment of the rotating body in the front-back-direction on the basis of fluctuation amount of a tilt angle.
Figure 8B:
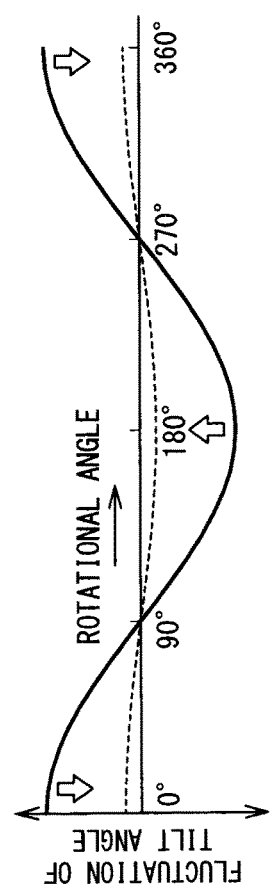
Figure 8C:
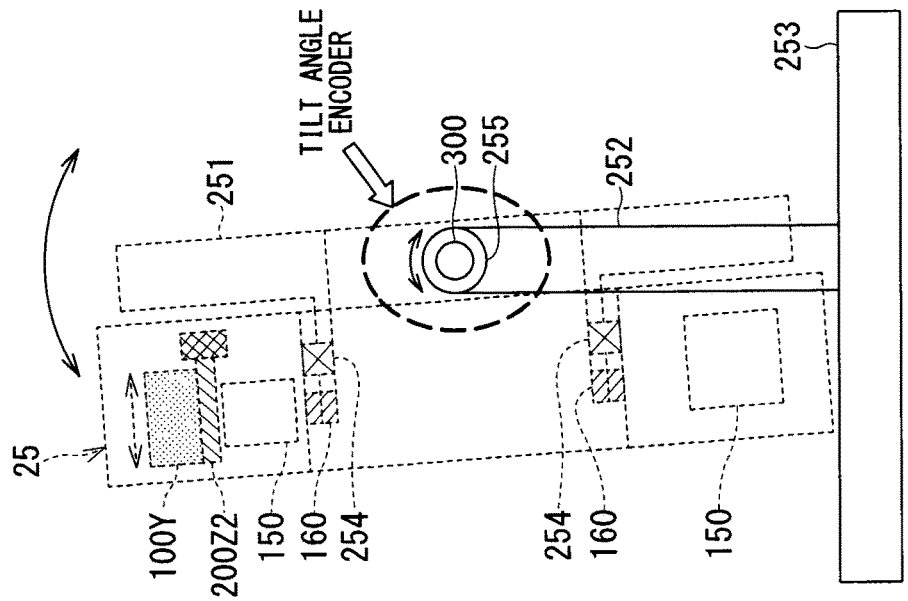

FIG. 8A to FIG. 8C are diagrams for explaining the concept of the balance adjustment of the rotating body 25 in the front-back-direction on the basis of the fluctuation of the tilt angle. FIG. 8A is a diagram illustrating a monitoring value of a tilt angle during the rotational motion under the condition where the tilt angle is set to zero degree. When the balance of the rotating body 25 in the front-back-direction is perfectly adjusted, the tilt angle becomes zero degree at any rotational angle. However, when the balance in the frontback-direction is imperfect, the rotating body 25 fluctuates around the center axis of the tilt bearing 255.

FIG. 8C is a diagram showing an example of outline arrangement of the scanning device 11 when viewed from the side, and is also a diagram corresponding to FIG. 2B. As mentioned above, the tilt bearing 255 is disposed between the fixed body 251 and the supporting structure 252, and the rotating body 25 and the fixed body 251 are configured to integrally turn in the tilt direction around the tilt bearing 255. The tilt angle encoder 300 is disposed adjacent to the tilt bearing 255, and the monitoring value of the tilt angle outputted from the tilt angle encoder 300. When the balance in the front-back direction is imperfect, the rotating body 25 and the fixed body 251 integrally fluctuate in the front-back direction while the rotating body 25 is rotating. As a result of this fluctuation, the monitoring value of the tilt angle detected by the tilt angle encoder 300 also fluctuates as illustrated with the solid curve line in FIG. 8A or FIG. 8B. The fluctuation-in-front-back-direction determination unit 504 determines the fluctuation of the rotating body 25 in the front-back direction, on the basis of such fluctuation of the tilt angle.

Figure 9A:
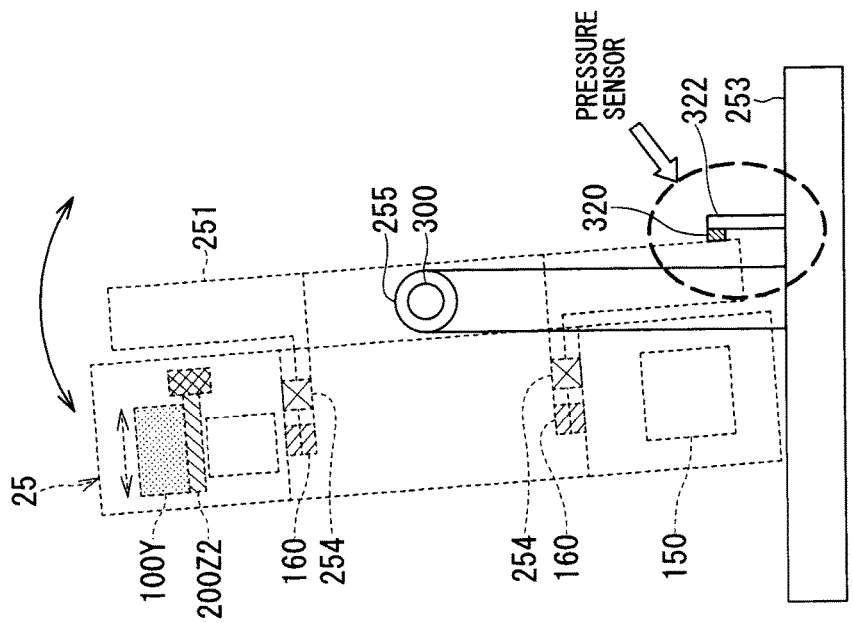
FIG. 9A is a diagram showing an example of detecting fluctuation in the front-back direction by using an optical sensor instead of a tilt angle encoder.
Figure 9B:
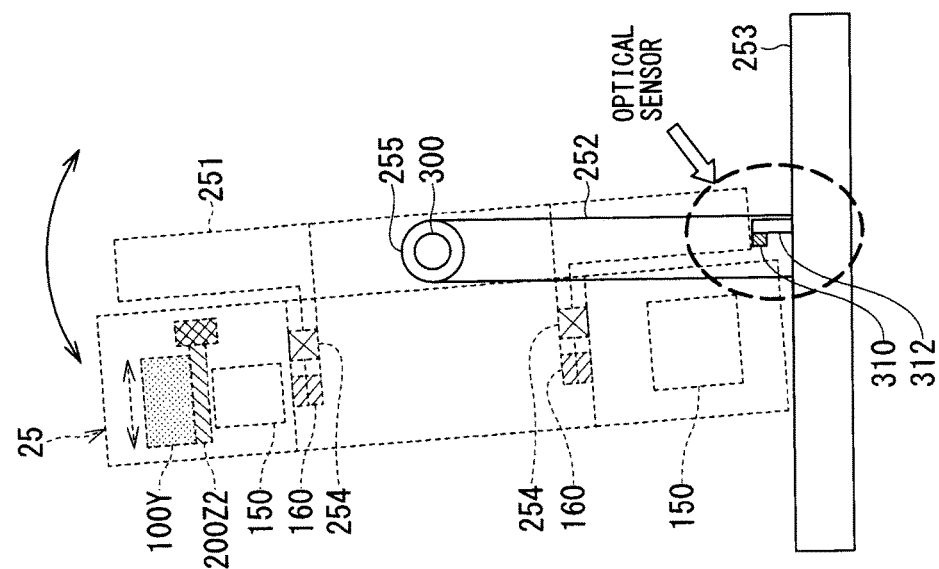
FIG. 9B is a diagram showing an example of detecting fluctuation in the front-back direction by using a pressure sensor instead of a tilt angle encoder.

The fluctuation of the rotating body 25 in the front-back direction can be detected not only by the tilt angle encoder 300 but also by other sensors. FIG. 9A and FIG. 9B are diagrams showing examples of detecting the fluctuation in the front-back direction by using other sensors except the tilt angle encoder 300.

FIG. 9A indicates an example of using an optical sensor 310 as a sensor. The optical sensor 310 is disposed, for example, on a supporting part 312 extending from the base 253. The optical sensor 310 irradiates light onto peripheral regions of the rotating surface of the rotating body 25 and detects fluctuation of distance between the optical sensor 310 and the rotating surface, for example. On the basis of the fluctuation of this distance, the fluctuation-in-front-back-direction determination unit 504 determines the fluctuation of the rotating body 25 in the front-back direction.

On the other hand, FIG. 9B indicates an example of using a pressure sensor 320 as a sensor. The pressure sensor 320 is disposed, for example, on a supporting part 322 extending from the base 253. The pressure sensor 320 is in contact with a part of the fixed body 251 and detects variation amount of pressure between the pressure sensor 320 and the fixed body 251. On the basis of this variation amount of pressure, the fluctuation-in-front-back-direction determination unit 504 determines the fluctuation of the rotating body 25 in the front-back direction. Although the fluctuation of the rotating body 25 or the fixed body 251 in the front-back direction is exaggerated in FIG. 9B and so on, actual fluctuation amount is approximately not more than 1 millimeter. Thus, the fluctuation in the front-back direction can be detected by even such a contact-type pressure sensor 320.

In addition, by irradiating light of the optical sensor 310 not onto the rotating body 25 but onto the fixed body 251, the fluctuation amount of the distance between the optical sensor 310 and the fixed body 251 can be also detected, and thus the fluctuation of the rotating body 25 in the front-back direction can be determined on the basis of this fluctuation of distance.

Returning to FIG. 6, in the step ST14, it is determined whether or not both of the fluctuation in the rotating surface determined in the step ST12 and the fluctuation in the front-back direction determined in the step ST13 are within a predetermined threshold value. When it is determined to be within the predetermined threshold value (YES in the step ST14), it is determined that the balance of the rotating body 25 is within a reference range and the balance adjustment processing is completed. On the other hand, when the fluctuation is larger than the predetermined threshold value (NO in the step ST14), the process proceeds to the step ST15 and the moving amount of the weight(s) is determined on the basis of the calculated fluctuation amount. As to the moving amount of the weight(s) in the rotating surface, it is determined by the weight-movement-in-rotating-surface determination unit 503. As to the moving amount of the weight(s) in the front-back direction, it is determined by the weight-movement-in-front-back-direction determination unit 505.

Various methods can be used for determining the moving amount of the weight(s) on the basis of the fluctuation. For example, the moving amount of the weight(s) can be determined by, (a) preliminarily storing the look-up table 506 in which the fluctuation with respect to the rotational angle and moving amount of the weight(s) necessary for reducing this fluctuation are associated with each other, and (b) then, referring to the look-up table 506 on the basis of the respective fluctuation determined in the step ST12 and the step ST13.

Assuming that the shape of the fluctuation is a sine wave shape as shown in FIG. 7B, FIG. 7C, FIG. 8A and FIG. 8B, for example, the parameters for determining the shape of the fluctuation are a peak value of fluctuation amount and a rotational angle corresponding to the peak value. In this case, input data to the look-up table 506 may be the peak value and the rotational angle. Meanwhile, output from the look-up table 506 may be information indicating, for example, which weight(s) should be moved, to which direction the weight(s) should be moved, and by what distance the weight(s) should be moved. Incidentally, the look-up table 506 can be preliminarily generated from database on the basis of analysis, simulation, experiments and so on.

Aside from the method of referring to the above look-up table 506, the moving amount of the weight(s) 100 which minimizes the fluctuation obtained by measurement can be determined by using various known searching methods.

When the moving amount of the weight(s) 100 is determined in the step ST15 as mentioned above, the weight(s) 100 is moved on the basis of the determined moving amount in the step ST16. More specifically, a control signal corresponding to the moving amount of the weight(s) 100 is transmitted from the console device 12 to the adjusting motor 201 of the weight moving mechanism 200, and the position of the weight(s) 100 is adjusted by driving the adjusting motor 201.

After this, returning to the step ST12, the processes from the step ST12 to the step ST16 are sequentially repeated until the fluctuation amount of the rotating body 25 becomes within the predetermined threshold value.

Incidentally, in the above explanation, it is assumed that the weight moving mechanisms 200 adjust the position of the weight(s) 100 which is specifically provided for the purpose of balance adjustment. However, the weight moving mechanisms 200 may adjust the position of one or a plurality of the rotating body components 150 so as to be served as a weight for balance adjustment. In this case, in the step ST16, the weight moving mechanism 200 moves the rotating body component 150 instead of the weight(s) 100. However, other processing is the same as the aforementioned processing.

As mentioned above, according to the X-ray CT apparatus 10 of the embodiment, the fluctuation of the rotating body 25 is determined on the basis of the monitoring signal outputted from the motor 160 for rotational motion originally provided on the X-ray CT apparatus 10 and the tilt angle encoder 300.

Therefore, it is not necessary to prepare measurement equipments exclusively for the balance adjustment at the time of adjusting the balance. In addition, work of installing such measurement equipments on the rotating body 25 and detaching them is not needed.

In addition, the X-ray CT apparatus 10 of this embodiment is configured to automatically determine the moving amount of the weight(s) 100 on the basis of the fluctuation and to automatically move the position of the weight(s) 100 on the basis of the determined moving amount. Therefore, the position adjustment of the weight(s) 100 can be accurately performed in a short time without relying on skills of an operator. In addition, it is not necessary for an operator to manually adjust the heaviness and position of the weight(s) like the conventional technology.

As just described, according to the X-ray CT apparatus 10 of the embodiment, rotational balance can be accurately adjusted in a short time without relying on skills of an operator.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
   a rotating body configured to house an X-ray tube which irradiates X-rays on an object;
   at least one weight configured to be housed in the rotating body and to adjust balance of the rotating body;
   a sensor configured to detect a fluctuation amount in a front-back direction approximately parallel to a rotating axis of the rotating body;
   processing circuitry configured to determine a moving amount of the weight based on the fluctuation amount in the front-back direction detected by the sensor;
   at least one weight moving mechanism configured to be housed in the rotating body and to move a position of the weight based on the moving amount determined by the processing circuitry; and
   a memory storing a look-up table in which the fluctuation amount and the moving amount of the weight necessary for reducing the fluctuation amount are associated with each other,
   wherein the processing circuitry is further configured to determine the moving amount of the weight by referring to the look-up table.

2. The X-ray CT apparatus according to claim 1,
   wherein the sensor is configured to detect a tilt angle of the rotating body; and
   the processing circuitry is configured to determine the moving amount of the weight using the fluctuation amount in the front-back direction based on the fluctuation amount of the tilt angle detected by the sensor.

3. The X-ray CT apparatus according to claim 2,
   wherein the sensor includes a tilt angle encoder configured to detect the tilt angle of the rotating body and is further configured to detect the tilt angle of the rotating body based on output from the tilt angle encoder.

4. The X-ray CT apparatus according to claim 1,
   wherein the sensor includes an optical sensor configured to irradiate light onto the rotating surface and is further configured to detect the fluctuation amount in the front-back direction by using the optical sensor.

5. The X-ray CT apparatus according to claim 1, further comprising a fixed body configured to be disposed on a rear side of the rotating body and to rotatably support the rotating body,
   wherein the sensor includes a pressure sensor disposed to be in contact with the fixed body and is further configured to detect the fluctuation amount in the front-back direction by using the pressure sensor.

6. The X-ray CT apparatus according to claim 1, further comprising a motor configured to rotate the rotating body,
   wherein the processing circuitry is further configured to determine a torque fluctuation amount based on a fluctuation amount of a drive current of the motor, determine a fluctuation amount in a rotating surface of the rotating body based on the torque fluctuation amount, and further determine the moving amount of the weight in the rotating surface based on the fluctuation amount in the rotating surface.

7. The X-ray CT apparatus according to claim 1,
   wherein the weight moving mechanism includes an adjusting motor and a motion convertor that converts rotational motion of the adjusting motor into linear motion.

8. The X-ray CT apparatus according to claim 7,
   wherein the motion convertor includes a ball screw and a slider meshing with the ball screw; and
   the weight is connected to the slider.

9. The X-ray CT apparatus according to claim 8, further comprising a worm gear having a self-locking function,
   wherein a worm wheel of the worm gear is connected to the ball screw and a worm of the worm gear is connected to a rotary shaft of the adjusting motor.

10. The X-ray CT apparatus according to claim 6, further comprising a plurality of components housed in the rotating body for obtaining the X-ray projection data, wherein at least one of the plurality of components serves as the weight;
    wherein the weight moving mechanism is further configured to move the at least one of the plurality of components in a predetermined radial direction in the rotating surface of the rotating body and to move the at least one of the plurality of components in the front-back direction orthogonal to the rotating surface.

11. The X-ray CT apparatus according to claim 6, further comprising a first weight, a second weight, a first weight moving mechanism, and a second weight moving mechanism,
    wherein the first weight moving mechanism is configured to move the first weight in a predetermined racial direction in the rotating surface, and the second weight moving mechanism is configured to move the second weight in the front-back direction orthogonal to the rotating surface.

* * * * *